United States Patent
Hara et al.

(10) Patent No.: US 8,181,524 B2
(45) Date of Patent: May 22, 2012

(54) ULTRASONIC STRESS MEASUREMENT METHOD AND DEVICE

(75) Inventors: Nobuo Hara, Osaka (JP); Yohei Takechi, Osaka (JP); Yutaka Omori, Osaka (JP)

(73) Assignee: Panasonic Corporation, Osaka (JP)

( * ) Notice: Subject to any disclaimer, the term of this patent is extended or adjusted under 35 U.S.C. 154(b) by 349 days.

(21) Appl. No.: 12/646,223

(22) Filed: Dec. 23, 2009

(65) Prior Publication Data

US 2010/0162817 A1    Jul. 1, 2010

(30) Foreign Application Priority Data

Dec. 26, 2008 (JP) ................................. 2008-332536

(51) Int. Cl.
*G01N 29/14* (2006.01)
(52) U.S. Cl. ................. 73/587; 73/579; 73/627; 73/630
(58) Field of Classification Search .................... 73/587, 73/577, 579, 597, 627, 630, 783, 787, 802
See application file for complete search history.

(56) References Cited

U.S. PATENT DOCUMENTS

| | | | |
|---|---|---|---|
| 6,478,875 B1 * | 11/2002 | Sampath et al. | 118/712 |
| 6,914,215 B2 * | 7/2005 | Davis et al. | 219/121.85 |
| 7,423,287 B1 * | 9/2008 | U'Ren et al. | 257/48 |
| 7,546,777 B2 * | 6/2009 | Bitto et al. | 73/861.355 |
| 2004/0262276 A1 * | 12/2004 | Davis et al. | 219/121.85 |
| 2009/0114019 A1 * | 5/2009 | Fatemi et al. | 73/587 |
| 2009/0301197 A1 * | 12/2009 | De Smet | 73/587 |

FOREIGN PATENT DOCUMENTS

JP    2004-77460    3/2004

* cited by examiner

*Primary Examiner* — J M Saint Surin
(74) *Attorney, Agent, or Firm* — Wenderoth, Lind & Ponack, L.L.P.

(57) ABSTRACT

The present invention relates to an ultrasonic stress measurement method of measuring a residual stress of a measuring target layer in a measuring object using an ultrasonic wave, the method comprising, setting a plurality of vibration modes according to a number of degree of freedom of the measuring target layer in the measuring object, performing, for each vibration mode, a measurement operation of emitting an ultrasonic wave corresponding to the set vibration mode to the measuring target layer, receiving the ultrasonic wave reflected by the measuring target layer, and measuring an eigenfrequency of the measuring target layer, and measuring the residual stress of the measuring target layer based on plural measurement data of the eigenfrequency with respect to each vibration mode obtained by the measurement operation. The residual stress of the measuring object thus can be measured at higher accuracy.

9 Claims, 5 Drawing Sheets

ULTRASONIC STRESS MEASUREMENT METHOD AND DEVICE

RELATED ART

The present invention relates to an ultrasonic stress measurement method and device for measuring a residual stress of a measuring object having a layered structure using an ultrasonic wave.

In a rechargeable battery used in an electronic device such as a portable telephone, improvement in electrical characteristics, conserving characteristics, and cycle characteristics at the time of charging and discharging, and reduction in a battery volume are desired. In particular, since the rechargeable battery has a property of expanding by repeating charging and discharging, the battery volume increases as the number of charging and discharging times increases, and the battery volume sometimes deviates from a standard dimension of the rechargeable battery. The residual stress of an interior of the rechargeable battery is desirably measured and controlled to suppress the increase of the battery volume.

A method of non-destructively measuring the residual stress includes a method of obtaining a residual stress from change of interatomic distances, a method of obtaining a residual stress from a magnetic distortion when magnetized, and a method of obtaining a residual stress from change in propagation speed of the ultrasonic wave (hereinafter referred to as an acoustoelastic method).

Figure 5:
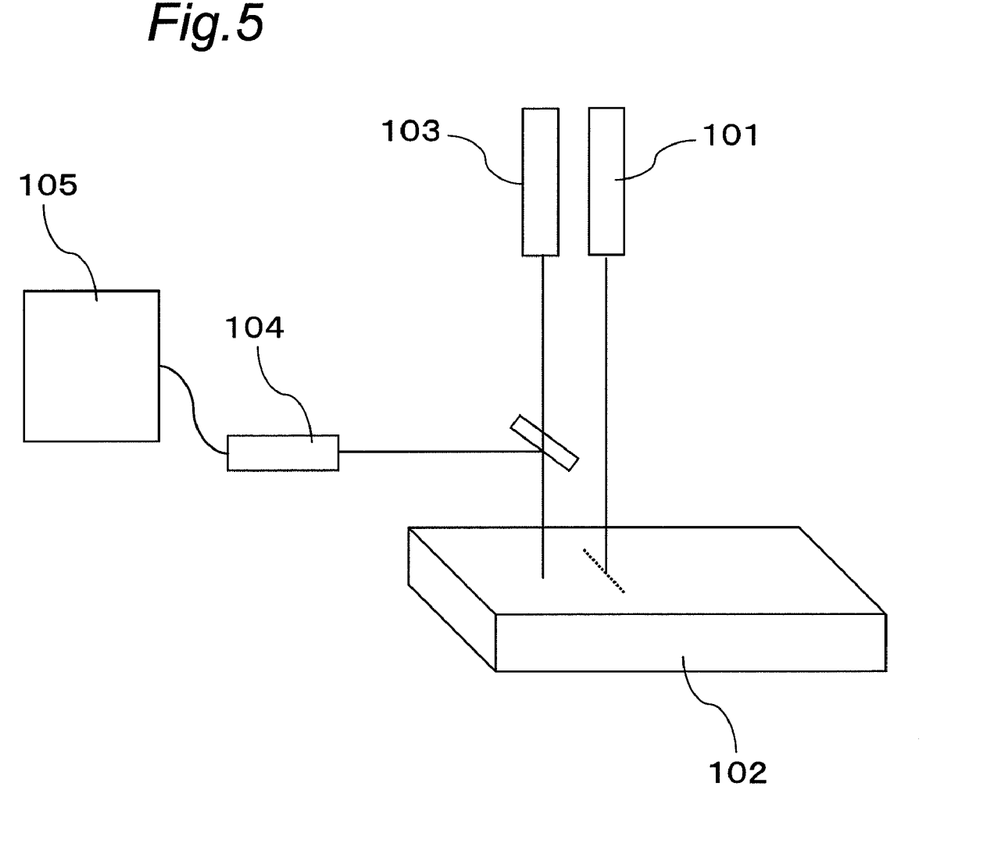
FIG. 5 is a schematic view of a conventional ultrasonic stress measurement device.

A birefringent acoustoelastic method is known as one acoustoelastic method. The birefringent acoustoelastic method is a method of measuring an average residual stress in a thickness direction of a measuring object by propagating the ultrasonic wave in the thickness direction of the measuring object. FIG. 5 is a schematic view showing a configuration of a conventional ultrasonic stress measurement device using such a birefringent acoustoelastic method (see e.g., Patent Document 1: Japanese Unexamined Patent Publication No. 2004-077460).

In the conventional ultrasonic stress measurement device shown in FIG. 5, an ultrasonic wave generation laser 101 emits two laser beams of different frequencies, so that ultrasonic waves, namely longitudinal wave, displacement transverse wave in a rolling direction, and displacement transverse wave in a width direction are generated in a measuring object 102. Each of such ultrasonic waves is reflected at a bottom surface of the measuring object 102, and ultrasonically vibrates an ultrasonic wave detection position at a surface of the measuring object 102. When a laser beam is emitted from an ultrasonic wave detection laser 103 to the ultrasonic wave detection position, a frequency of the laser beam changes as a result of Doppler shift caused by the ultrasonic vibration. Such change in frequency is detected by an interferometer 104. A computer 105 obtains an internal temperature of the measuring object 102 based on the change in frequency by the longitudinal wave detected by the interferometer 104, and calculates a sound velocity based on the change in frequency by the two transverse waves detected by the interferometer 104. Thereafter, the computer 105 substitutes the internal temperature and the sound velocity to a formula that uses a sound velocity ratio method for calculation. The residual stress of the measuring object 102 is thereby obtained.

SUMMARY OF THE INVENTION

However, the conventional ultrasonic stress measurement device has an issue in that the residual stress cannot be measured at high accuracy due to an influence of anisotropy (acoustic anisotropy) of a material itself of the measuring object. In other words, the anisotropy (acoustic anisotropy) of the material itself of the measuring object depends on a thickness of the material, the incident angle of the ultrasonic wave, and the like. Thus, if the measuring object has a multi-layered structure, the anisotropy changes due to variation in a thickness of each layer and the like. The change in anisotropy influences the propagation speed of the ultrasonic wave. Thus, measurement error due to the anisotropy occurs in the acoustoelastic method of obtaining stress from the change in the propagation speed of the ultrasonic wave. Therefore, the residual stress cannot be measured at high accuracy in the conventional ultrasonic stress measurement device that uses the birefringent acoustoelastic method.

Therefore, the present invention has been devised to improve the issues, and an object thereof is to provide an ultrasonic stress measurement method and device capable of measuring the residual stress of the measuring object at higher accuracy.

In order to achieve the above-mentioned object, the present invention provides the following configuration.

According to a first aspect of the present invention, there is provided an ultrasonic stress measurement method of measuring a residual stress of a measuring target layer in a measuring object using an ultrasonic wave; the method comprising:

setting a plurality of vibration modes according to a number of degree of freedom of the measuring target layer;

performing, for each vibration mode, a measurement operation of emitting an ultrasonic wave corresponding to the set vibration mode to the measuring target layer, receiving the ultrasonic wave reflected by the measuring target layer, and measuring an eigenfrequency of the measuring target layer; and measuring the residual stress of the measuring target layer based on plural measurement data of the eigenfrequency with respect to each vibration mode obtained by the measurement operation.

According to a second aspect of the present invention, there is provided the ultrasonic stress measurement device according to the eighth aspect, further comprising:

an acoustic lens for converging the ultrasonic wave reflected by the measuring target layer to a converging position; and an ultrasonic wave shielding unit, in which a pin hole is formed at the converging position, for passing the ultrasonic wave reflected by the measuring target layer through the pin hole to be received by the ultrasonic wave receiving unit, and shielding the ultrasonic wave reflected at portions other than the measuring target layer.

According to the ultrasonic stress measurement method and device of the present invention, the residual stress of the measuring object can be measured at higher accuracy.

BRIEF DESCRIPTION OF THE DRAWINGS

These and other aspects and features of the present invention will become clear from the following description taken in conjunction with the preferred embodiments thereof with reference to the accompanying drawings, in which.

DETAILED DESCRIPTION OF INVENTION

Embodiments of the present invention will be described below with reference to the drawings. Like reference symbols are denoted for the like configurations, and the description thereof will not be given in the description of the embodiment of the present invention.

《Embodiment》

A configuration of an ultrasonic stress measurement device according to an embodiment of the present invention will be described.

Figure 1:
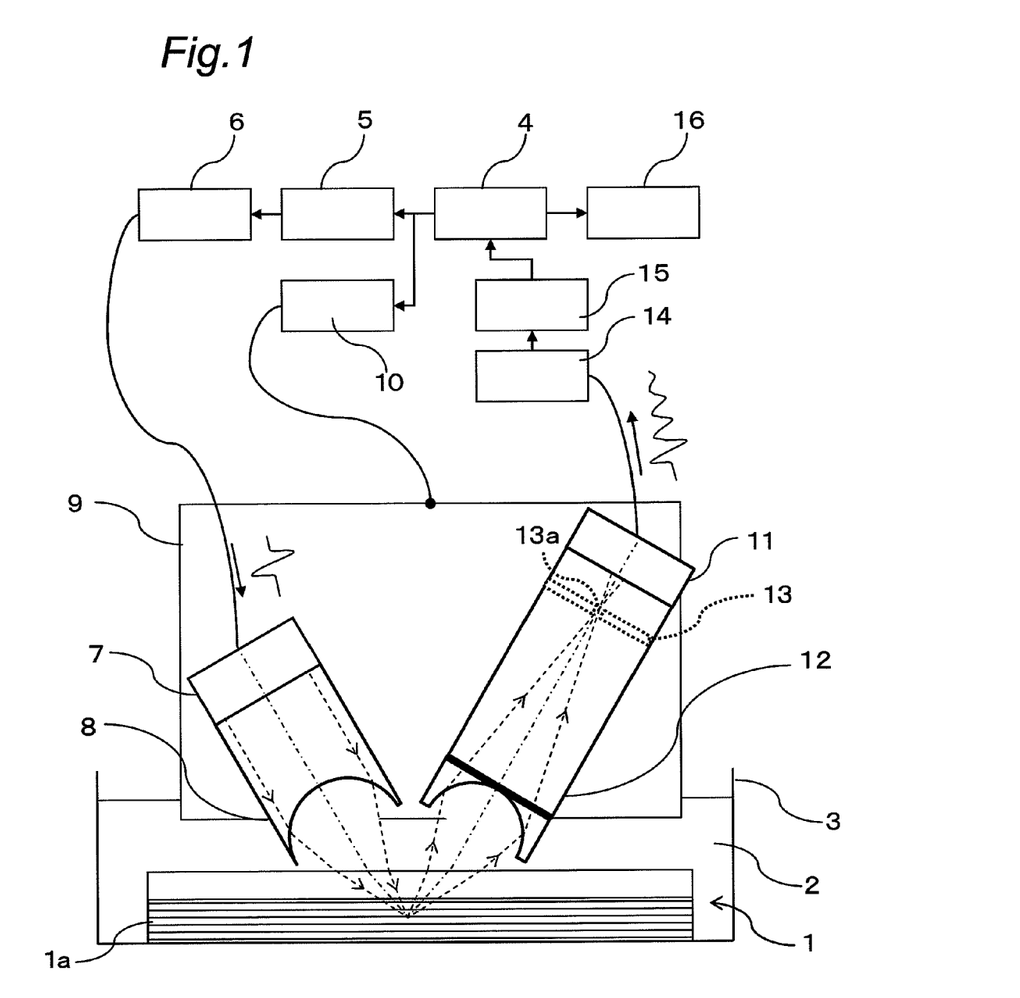
FIG. 1 is a schematic view of an ultrasonic stress measurement device according to an embodiment of the present invention.

FIG. 1 is a schematic view of an ultrasonic stress measurement device according to the present embodiment.

In FIG. 1, a measuring object 1, which residual stress is to be measured by the ultrasonic stress measurement device according to the present embodiment, is arranged in a container 3 filled with a coupling agent 2.

The measuring object 1 has a multi-layered structure such as a rechargeable battery including a lithium ion battery used in an electronic device such as a portable telephone. The lithium ion battery has a multi-layered structure using a lithium cobaltate for a positive electrode plate and graphite for a negative electrode plate, respective electrode plates being stacked in plurals.

The coupling agent 2 stabilizes the propagation speed of the ultrasonic wave. Glycerin, propylene glycol, water, oil, gel, and the like can be used for the coupling agent 2.

Various conditions such as material, internal structure (layer thickness of each layer etc.), restraining condition, and the like of the measuring object 1 are obtained in advance using measurement data, design data, and the like by an X-ray CT device and the like. The data of various conditions are saved (stored) in advance in a computer 4, which serves as a stress measurement unit, by an input operation etc. of the user. The restraining condition of the present embodiment is a condition for physically restraining the measuring object 1. For instance, if two sides of a rectangular measuring object are fixed and two sides are free, the restraining condition of the measuring object will be "two sides are restrained".

The computer 4 defines (sets) a predicting eigenfrequency (vibration mode: basic vibration, double vibration, triple vibration, . . . ) of a measuring target layer 1a of the measuring object 1 by the number of degree of freedom of the measuring target layer 1a based on the data of the various conditions of the measuring object 1. The degree of freedom of the measuring target layer 1a means unknown items related to the measuring target layer 1a such as width, length, area density, stress per unit length, and the like of the measuring target layer 1a. For instance, if two items of the width and the length of the measuring target layer 1a are unknown, the computer 4 sets two vibration modes as vibration modes of the predicting eigenfrequency.

After the setting, the computer 4 outputs a digital signal corresponding to the set vibration mode. The digital signal is converted to an electrical signal by a D/A converter 5 and a transmission pulse 6, and inputted to a first flaw detector 7, which serves as an ultrasonic wave emitting unit.

The first flaw detector 7 converts the electrical signal to an ultrasonic signal. If the number of degree of freedom of the measuring target layer 1a is two or more, two or more vibration modes are set, as described above. In this case, the first flaw detector 7 is arranged in plurals since the range of vibration mode that can be responded with one first flaw detector 7 is small, and the eigenfrequency of each first flaw detector 7 is preferably corresponded to one of the plurality of vibration modes. In this case, the electrical signal corresponding to the vibration mode should be inputted to the first flaw detector 7 having the eigenfrequency corresponding to the vibration mode set by the computer 4.

The ultrasonic wave emitted from the first flaw detector 7 is converged by a first acoustic lens 8 disposed at a distal end of the first flaw detector 7. The converging position of the ultrasonic wave is determined from conditions such as design information of the first acoustic lens 8, arrangement relation between the first flaw detector 7 and the measuring object 1, composition of each member (measuring object 1, coupling agent 2, etc.) and the like. The first flaw detector 7 is held by a flaw detector head 9. The flaw detector head 9 is moved (position adjusted) so that the converging position is positioned inside the measuring target layer 1a by the control of a control unit 10. The control unit 10 moves (position adjusts) the flaw detector head 9 based on the digital signal outputted by the computer 4.

As described above, the ultrasonic wave emitted from the first flaw detector 7, with the flaw detector head position adjusted, is reflected at a surface of the measuring target layer 1a. The reflected ultrasonic wave enters a second acoustic lens 12, which is installed at a distal end of a second flaw detector 11 serving as an ultrasonic wave receiving unit, while diffusing, and is converged by the second acoustic lens 12. An ultrasonic wave shielding plate 13, which serves as an ultrasonic wave shielding unit, is arranged inside the second acoustic lens 12. The ultrasonic wave shielding plate 13 is formed with a pin hole 13a. The second flaw detector 11 and the second acoustic lens 12 are held by the flaw detector head 9 so that the converging position of the ultrasonic wave converged by the second acoustic lens 12 matches the pin hole 13a of the ultrasonic wave shielding plate 13. In other words, each unit and each device are adjusted such that the diameter of the pin hole 13a and the converging diameter of the ultrasonic wave reflected by the measuring target layer 1a become equal.

The ultrasonic wave converged by the second acoustic lens 12 and passed through the pin hole 13a is received by the second flaw detector 11, and converted to an electrical signal. The electrical signal is amplified by an amplifier 14, converted to a digital signal by an A/D converter 15, and inputted to the computer 4. The computer 4 measures the eigenfrequency of the measuring target layer 1a based on the inputted digital signal.

The computer 4 performs the above-mentioned operation while changing the predicting eigenfrequency (vibration mode) by the number of degree of freedom of the measuring target layer 1a, and calculates the residual stress of the measuring target layer 1a based on the data acquired herewith. The calculation method will be described in detail below. The data etc. calculated by the computer 4 are appropriately displayed on a display 16.

A flow of ultrasonically stress measuring the residual stress of the measuring object 1 according to the present embodiment will be described below.

Figure 2:
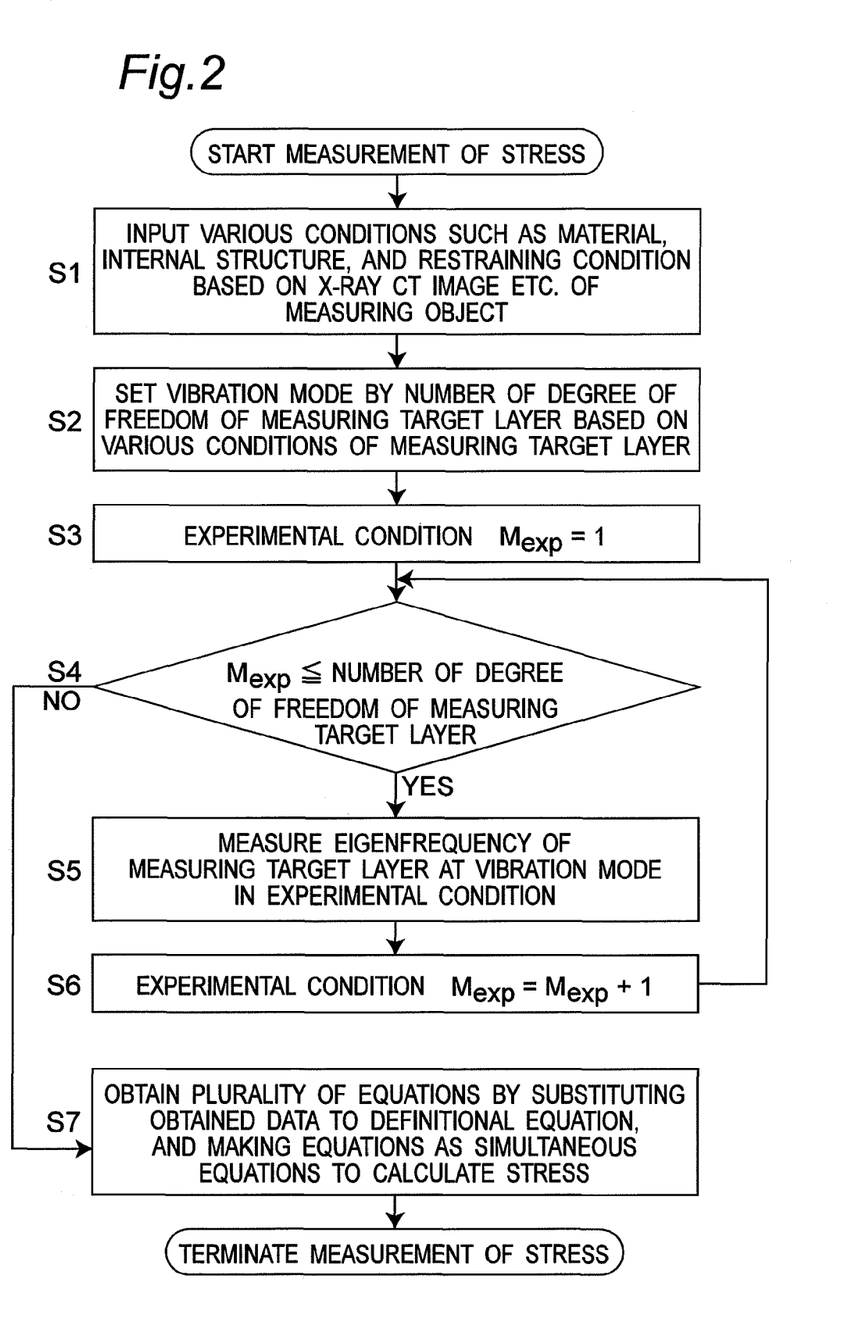
FIG. 2 is a flowchart showing an ultrasonic stress measurement method according to the embodiment of the present invention.

FIG. 2 is a flowchart showing the ultrasonic stress measurement method according to the present embodiment.

First, various conditions such as material, internal structure (layer thickness etc.), restraining condition, and the like of the measuring object 1 having a multi-layered structure are inputted and stored in the computer 4 in advance from design information or the X-ray CT image of the measuring object 1 (step S1). The operation described below is mainly performed by the computer 4 unless particularly stated.

The predicting eigenfrequency (vibration mode: basic vibration, double vibration, triple vibration, with respect to one measuring target layer 1a is set (defined) by the number of degree of freedom of the measuring target layer 1a based on the stored various conditions of the measuring object 1 (step S2). For instance, if the measuring target layer 1a is a rectangular film and the four sides of the rectangular film are fixed (restrained), the definitional equation of the eigenfrequency $\omega_{m,n}$ of the measuring target layer 1a is expressed as equation 1 below.

$$\omega_{m,n} = \sqrt{\frac{T}{\rho}\pi^2\left(\frac{m^2}{a^2} + \frac{n^2}{b^2}\right)} \quad [\text{rad/s}] \quad \text{(equation 1)}$$

In equation 1, "a" is a length of a short side of the rectangular film which is the measuring object, "b" is a length of a long side, "ρ" is a area density of the film, "T" is a stress per unit area applied on the film, "m" is a vibration mode in a X-direction of a surface of the rectangular film, and "n" is a vibration mode in a Y-direction of a surface of the rectangular film. In the present embodiment, the stress "T" defined in equation 1 becomes a residual stress of the rectangular film which is the measuring object. Therefore, the residual stress of the measuring object can be obtained by obtaining the stress "T" using equation 1 and the like.

If there are "M" unknowns ("M" is a natural number), all unknowns can be generally calculated by making or more equations as simultaneous equations. For instance, if the length "a" of the short side, the length "b" of the long side, the area density "ρ", and the stress are the unknowns in equation 1, the experimental conditions "$M_{exp}$" are prepared in four ways, a data obtained from such experimental conditions are substituted to equation 1 to obtain four equations, and such equations are made as simultaneous equations so that four unknowns can be calculated. The length "a" of the short side, the length "b" of the long side, and the area density "ρ" are preferably calculated at the same time as the stress "T" to measure the stress "T" at high accuracy.

After step S2, the eigenfrequency "$\omega_{m,n}$" of the measuring target layer 1a is calculated with the experimental condition "$M_{exp}$" as "$M_{exp}$"=1 (step S3). The experimental condition "$M_{exp}$" is prepared in advance by the number of degree of freedom of the measuring target layer 1a. Specifically, a combination of the X-direction vibration mode "m" and the Y-direction vibration mode "n" is set for every experimental condition. If there are four experimental conditions, a combination of (m=1, n=2) is set for $M_{exp}$=1, (m=2, n=2) is set for $M_{exp}$=2, (m=2, n=1) is set for $M_{exp}$=3, and (m=2, n=3) is set for $M_{exp}$=4. Here, "m=1" means reference vibration, "m=2" means double vibration, and "m=3" means triple vibration. Similarly, "n=1" means reference vibration, "n=2" means double vibration, and "n=3" means triple vibration.

The computer 4 then determines whether or not the experimental condition "$M_{exp}$" is smaller than or equal to the number of degree of freedom of the measuring target layer 1a (step S4).

If the experimental condition "$M_{exp}$" is smaller than or equal to the number of degree of freedom of the measuring target layer 1a, the eigenfrequency "$\omega_{m,n}$" of the measuring target layer 1a is measured at the vibration mode (combination of X-direction vibration mode "m" and Y-direction vibration mode "n") in the experimental condition "$M_{exp}$" (step S5). For instance, if the experimental condition is "$M_{exp}$=1", the ultrasonic wave corresponding to the vibration mode (m=1, n=2) is emitted from the first flaw detector 7, and the eigenfrequency "$\omega_{m,n}$" of the measuring target layer 1a is measured based on the ultrasonic wave reflected by the measuring target layer 1a.

The experimental condition "$M_{exp}$" is incremented (calculation of increasing the value of the variable by one), and the process returns to step S4 (step S6). The operations of steps S4 to S6 are repeated until the "$M_{exp}$" becomes greater than the number of degree of freedom of the measuring target layer 1a, so that the measurement data of the eigenfrequency "$\omega_{m,n}$" of the measuring target layer 1a is obtained in plurals.

When the experimental condition "$M_{exp}$" becomes greater than the number of degree of freedom of the measuring target layer 1a, the measurement of the eigenfrequency of the measuring target layer 1a is terminated. Thereafter, the plurality of obtained measurement data are substituted to equation 1 to obtain a plurality of equations, and such equations are made as simultaneous equations to calculate the stress "T" (step S7). Here, the definitional equation is made as simultaneous equations by only the number of unknown items, and thus not only the stress "T", but all other unknown items can be calculated. For instance, if the lengths of the short side and the long side of the rectangular film which is the measuring target layer 1a are unknown, the lengths of the short side and the long side of the rectangular film can be calculated at the same time as the stress "T". The stress "T" (residual stress) thus can be measured at higher accuracy.

Steps S1 to S7 are respectively performed on all the layers of the measuring object 1, so that the residual stress of each layer of the measuring object 1 having a multi-layered structure can be calculated. An internal residual stress distribution of the measuring object 1 can be obtained by calculating all the residual stress of each layer of the measuring object 1.

A waveform of the electrical signal generated by the transmission pulse 6 will now be described.

Figure 3A:
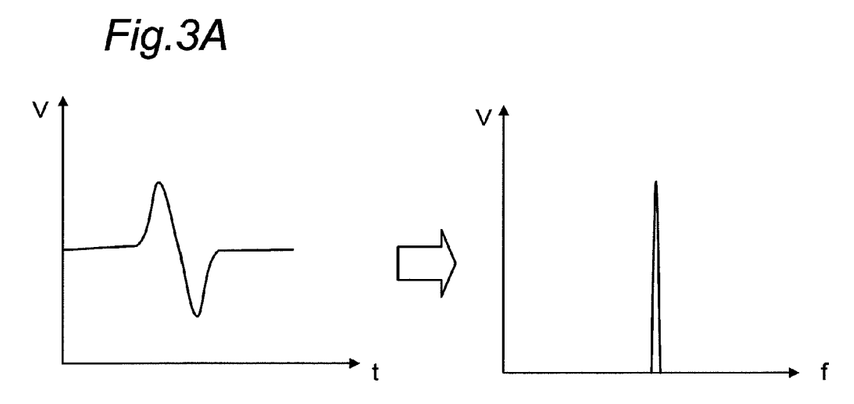
FIG. 3A is a view showing a waveform of a general pulse signal.
Figure 3B:
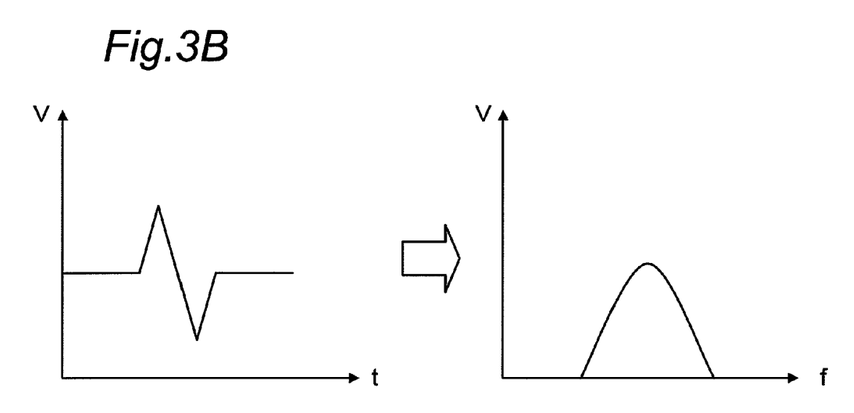
FIG. 3B is a view showing a waveform of an electrical signal generated by a transmission pulse according to the embodiment of the present invention.

FIG. 3A is a view showing a waveform of a general pulse signal, and FIG. 3B is a view showing the waveform of the electrical signal generated by the transmission pulse in the present embodiment. The left diagrams of FIGS. 3A and 3B are diagrams showing change in voltage value (V) with respect to time (t), and the right diagrams of FIGS. 3A and 3B are diagrams showing change in voltage value (V) with respect to frequency (f).

As shown in FIG. 3A, the waveform of the electrical signal of a general pulse has a perfect pulse shape. On the contrary, in the present embodiment, the electrical signal generated by the transmission pulse 6 does not have a perfect pulse shape, and is an electrical signal having a frequency of a wide band, as shown in FIG. 3B. Even when the predicting eigenfrequency of the measuring target layer 1a and the actual eigenfrequency greatly differ, the possibility that resonance occurs between the layers becomes high, and the influence between the layers (between the measuring target layer 1a and the layer in the vicinity thereof) of the measuring object 1 which is a multi-layered structure becomes small.

In the present embodiment, the residual stress of the measuring target layer 1a is calculated according to the flowchart shown in FIG. 2. Here, if an inter-layer distance between the measuring target layer 1a and the layer in the vicinity thereof is short, the ultrasonic wave reflected by the layer in the vicinity also has a possibility of being received by the second flaw detector 11. In this case, the stress cannot be measured at high accuracy. In the present embodiment, the ultrasonic wave shielding plate 13 including the pin hole 13a is arranged to alleviate the influence of the ultrasonic wave reflected by the layer other than the measuring target layer 1a. In other words, the ultrasonic wave reflected by the measuring target layer 1a passes the ultrasonic wave shielding plate through the pin hole 13a, and the ultrasonic wave reflected by the layer other than the measuring target layer 1a is shielded by the ultrasonic wave shielding plate 13. Therefore, the residual stress can be measured at higher accuracy.

A preferred arrangement of the pin hole 13a will now be described.

Figure 4A:
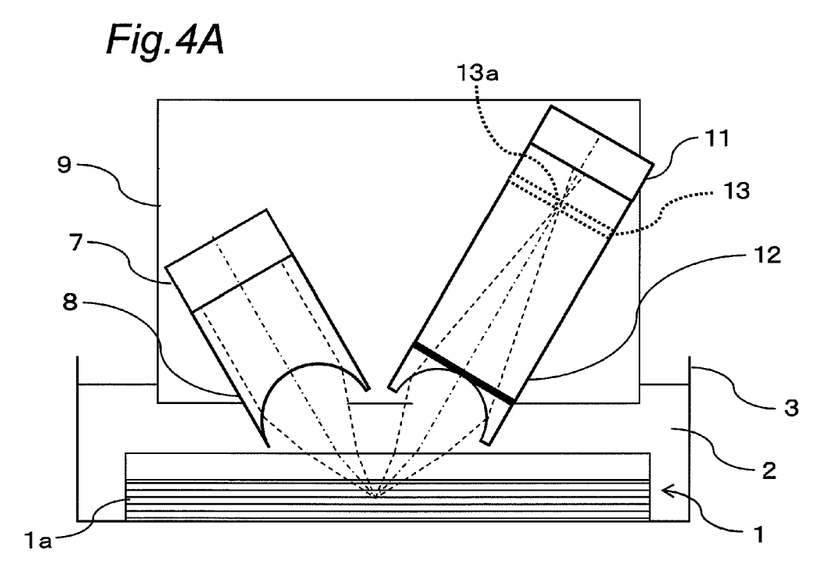
FIG. 4A is a schematic view showing a state in which an ultrasonic wave emitted from a first flaw detector and reflected by a measuring target layer passes through a pin hole in the ultrasonic stress measurement device according to the embodiment of the present invention.
Figure 4B:
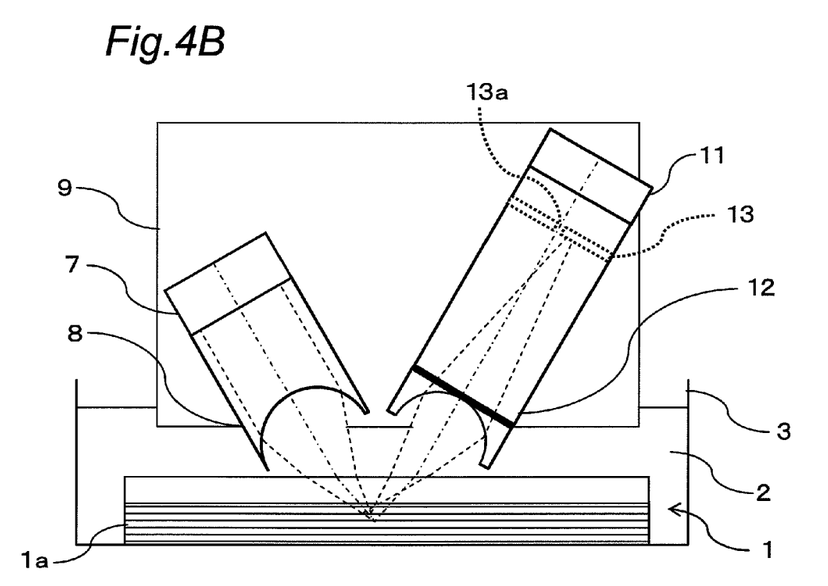
FIG. 4B is a schematic view showing a state in which the ultrasonic wave emitted from the first flaw detector and reflected by a layer other than the measuring target layer is shielded by an ultrasonic wave shielding plate in the ultrasonic measurement device according to the embodiment of the present invention.

FIG. 4A is a schematic view showing a state in which the ultrasonic wave emitted from the first flaw detector 7 and reflected by the measuring target layer 1a passes through the pin hole in the ultrasonic measurement device according to the present embodiment, and FIG. 4B is a schematic view showing a state in which the ultrasonic wave emitted from the first flaw detector 7 and reflected by the layer other than the measuring target layer 1a is shielded by the ultrasonic wave shielding plate 13 in the ultrasonic measurement device according to the present embodiment.

With a focal length of the first acoustic lens 8 as F1, a focal length of the second acoustic lens 12 as F2, a distance from the second acoustic lens 12 to the pin hole 13a as F3, the sound velocity in the coupling agent 2 as V1, and the sound velocity in the material used for the second flaw detector 11 as V2, the pin hole 13a is preferably arranged to satisfy a relationship of equation 2 below.

$$\frac{1}{F2} = \frac{1}{F1} + \frac{V2/V1}{F3} \quad \text{(equation 2)}$$

With an opening diameter of the second acoustic lens 12 as D2, a diameter of the pin hole 13a as R3, and a smallest of the eigenfrequency of the measuring target layer 1a as $\omega_{min}$ a diameter of the pin hole 13a is preferably set to satisfy a relationship of equation 3 below.

$$R3 < \frac{V2}{\omega_{min}} \frac{F2}{D2} \quad \text{(equation 3)}$$

For instance, with the focal length F1 as 40 mm, the focal length F2 as 10 mm, the sound velocity V1 in the coupling agent 2 as 1500 m/s (water), the sound velocity V2 in the second acoustic lens 11 as 5900 m/s (fused silica), and the minimum eigenfrequency $\omega_{min}$ as 20 MHz, the distance F3 from the second acoustic lens 12 to the pin hole 13a is preferably 52.4 mm and the diameter R3 of the pin hole 13a is preferably smaller than 0.98 mm. If arranged in such a manner, the ultrasonic wave reflected by the measuring target layer 1a passes the pin hole 13a, as shown in FIG. 4A. The ultrasonic wave reflected by the layer other than the measuring target layer 1a can be shielded by the ultrasonic wave shielding plate 13, as shown in FIG. 4B. The high accuracy measurement of the residual stress having high SN ratio can be realized.

Therefore, according to the configuration of the present embodiment, the residual stress of each layer can be measured at high accuracy by carrying out analysis at the eigenfrequency with the vibration mode changed, even if the internal structure (measuring target layer 1a etc.) of the measuring object 1 cannot be accurately grasped. Furthermore, the internal structure (length of short side, length of long side, etc.) of the measuring object 1 calculated as an unknown item in addition to the residual stress can also be measured. The ultrasonic wave reflected by the layer other than the measuring target layer 1a can be shielded by the ultrasonic wave shielding plate 13. The measurement that is less likely to be influenced by the ultrasonic wave reflected by the layer other than the measuring target layer 1a thus can be carried out.

The present invention is not limited to the above embodiment, and may be implemented in various other modes. For instance, the measuring object 1 is arranged in the container 3 filled with the coupling agent 2, but the present invention is not limited thereto. The coupling agent 2 merely needs to be filled between the first flaw detector 7 and the measuring object 1, and between the measuring object 1 and the second flaw detector 11. Similar effects can be realized in this case as well.

In the present embodiment, the pin hole 13a of the ultrasonic wave shielding plate 13 is formed at the converging position of the ultrasonic wave converged by the second acoustic lens 12, but the present invention is not limited thereto. The pin hole 13a may be formed at the position other than the converging position. In this case, if the ultrasonic wave reflected by the measuring target layer 1a is completely shielded by the ultrasonic wave shielding plate 13, the ultrasonic stress measurement of the measuring target layer 1a will not be possible. A installing position of the pin hole 13a and a diameter of the pin hole 13a thus need to be set so that the ultrasonic wave reflected by the measuring target layer 1a is not completely shielded by the ultrasonic wave shielding plate 13.

The ultrasonic stress measurement method and device of the present invention enable the residual stress of the measuring object to be measured at higher accuracy, and thus are useful in measuring the residual stress of the measuring object having a layered structure such as a rechargeable battery and a mounting substrate.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

The disclosure of Japanese Patent Application No. 2008-332536 filed on Dec. 26, 2008 including specification, drawing and claims are incorporated herein by reference in its entirety.

The invention claimed is:

1. An ultrasonic stress measurement method of measuring a residual stress of a measuring target layer in a measuring object using an ultrasonic wave; the method comprising:
   setting a plurality of vibration modes according to a number of degree of freedom of the measuring target layer;
   performing, for each vibration mode, a measurement operation of emitting an ultrasonic wave corresponding to the set vibration mode to the measuring target layer, receiving the ultrasonic wave reflected by the measuring target layer, and measuring an eigenfrequency of the measuring target layer; and measuring the residual stress of the measuring target layer based on plural measurement data of the eigenfrequency with respect to each vibration mode obtained by the measurement operation.

2. The ultrasonic stress measurement method according to claim 1, wherein the residual stress of the measuring target layer is measured by substituting data of the eigenfrequency of the measuring target layer with respect to each vibration mode obtained by the measurement operation to a definitional equation for obtaining the eigenfrequency of the measuring target layer to obtain a plurality of equations, and making the equations as simultaneous equations.

3. The ultrasonic stress measurement method according to claim 1, wherein a number of vibration modes is equal to the number of degree of freedom of the measuring target layer.

4. The ultrasonic stress measurement method according to claim 1, wherein the measurement operation is an operation of measuring the eigenfrequency of the measuring target layer by emitting the ultrasonic wave corresponding to the set vibration mode so as to converge at the measuring target layer, converging the ultrasonic wave reflected by the measuring target layer in a pin hole formed at an ultrasonic wave shielding unit, and receiving only the ultrasonic wave passed through the pin hole.

5. The ultrasonic stress measurement method according to claim 4, wherein a diameter of the pin hole is equal to a converging diameter of the ultrasonic wave reflected by the measuring target layer.

6. The ultrasonic stress measurement method according to claim 1, wherein the vibration mode is set based on a material and a layer thickness of the measuring target layer.

7. The ultrasonic stress measurement method according to claim 1,
wherein the measuring object has a multi-layered structure configured by a plurality of layers;
the ultrasonic stress measurement method comprising:
performing the measurement of the residual stress for each of the plurality of layers; and
obtaining an internal stress distribution of the measuring object based on the measurement results of the residual stress of each of the plurality of layers.

8. An ultrasonic stress measurement device for measuring a residual stress of a measuring target layer in a measuring object using an ultrasonic wave; the ultrasonic stress measurement device comprising:
an ultrasonic wave emitting unit for emitting, to the measuring target layer, a plurality of ultrasonic waves corresponding to a plurality of vibration modes set according to a number of degree of freedom of the measuring target layer;
an ultrasonic wave receiving unit for receiving each ultrasonic wave reflected by the measuring target layer; and
a stress measurement unit for measuring an eigenfrequency of the measuring target layer based on each ultrasonic wave received by the ultrasonic wave receiving unit, and measuring the residual stress of the measuring target layer based on plural measurement data of the eigenfrequency obtained by the measurement.

9. The ultrasonic stress measurement device according to claim 8, further comprising:
an acoustic lens for converging the ultrasonic wave reflected by the measuring target layer to a converging position; and
an ultrasonic wave shielding unit, in which a pin hole is formed at the converging position, for passing the ultrasonic wave reflected by the measuring target layer through the pin hole to be received by the ultrasonic wave receiving unit, and shielding the ultrasonic wave reflected at portions other than the measuring target layer.

* * * * *